(12) United States Patent
Lynch

(10) Patent No.: US 12,419,576 B2
(45) Date of Patent: Sep. 23, 2025

(54) WEARABLE ARTICLE

(71) Applicant: PREVAYL INNOVATIONS LIMITED, Wilmslow (GB)

(72) Inventor: Michael John Lynch, Manchester (GB)

(73) Assignee: Prevayl Innovations Limited, Wilmslow (GB)

(*) Notice: Subject to any disclaimer, the term of this patent is extended or adjusted under 35 U.S.C. 154(b) by 71 days.

(21) Appl. No.: 17/795,070

(22) PCT Filed: Feb. 9, 2021

(86) PCT No.: PCT/GB2021/050285
§ 371 (c)(1),
(2) Date: Jul. 25, 2022

(87) PCT Pub. No.: WO2021/160998
PCT Pub. Date: Aug. 19, 2021

(65) Prior Publication Data
US 2023/0071908 A1 Mar. 9, 2023

(30) Foreign Application Priority Data
Feb. 10, 2020 (GB) .................................... 2001804

(51) Int. Cl.
*A61B 5/00* (2006.01)
*A41D 1/00* (2018.01)
*G01D 5/20* (2006.01)

(52) U.S. Cl.
CPC ............ *A61B 5/6805* (2013.01); *A41D 1/002* (2013.01); *A61B 5/0002* (2013.01);
(Continued)

(58) Field of Classification Search
CPC ... A61B 5/6805; A61B 5/0002; A61B 5/6804; A61B 5/684; A61B 2562/0219;
(Continued)

(56) References Cited

U.S. PATENT DOCUMENTS 8,271,662 B1 * 9/2012 Gossweiler, III ....... H04W 4/80
709/227
9,554,721 B1 1/2017 Zikov et al.
(Continued)

FOREIGN PATENT DOCUMENTS

CN 204351118 U 5/2015
CN 206166913 U 5/2017
(Continued)

OTHER PUBLICATIONS

Siyu E (Technical Report No. UCB/EECS-2012-153, Jun. 1, 2012, 21 pages) (Year: 2012).
(Continued)

*Primary Examiner* — Quan Zhen Wang
*Assistant Examiner* — Rajsheed O Black-Childress
(74) *Attorney, Agent, or Firm* — Haley Guiliano LLP

(57) ABSTRACT

The wearable article 200 comprises an electronics module 100. An electronics module holder 203 holds the electronics module 100. A visual marker 205 is located on an outside surface of the wearable article 200 at a position corresponding to the electronics module holder 203. The module 100 comprises a housing, and a processor 101 and electronics component 111 disposed within the housing. The electronics component 111 detects an object being brought into proximity with the electronics module 100. The visual marker 205 indicates the location of the electronics component 111 in the electronics module holder 203. The electronics component 111 generates a signal in response to the object being brought into the vicinity of the visual marker 205. The processor 101 is arranged to receive the signal generated by the electronics component 111 and is arranged to perform an action in response to receiving the signal.

20 Claims, 7 Drawing Sheets

(52) U.S. Cl.
CPC .............. *A61B 5/6804* (2013.01); *G01D 5/20* (2013.01); *A61B 5/684* (2013.01); *A61B 2562/0219* (2013.01); *A61B 2562/0257* (2013.01); *A61B 2562/08* (2013.01)

(58) Field of Classification Search
CPC ........ A61B 2562/0257; A61B 2562/08; A61B 5/02055; A61B 5/1118; A61B 5/256; A61B 5/6802; A41D 1/002; A41D 13/1281; G01D 5/20
See application file for complete search history.

(56) References Cited

U.S. PATENT DOCUMENTS

| | | | |
|---|---|---|---|
| 10,499,849 | B1 | 12/2019 | Chuang |
| 11,557,397 | B2 | 1/2023 | Crofts et al. |
| 2004/0171956 | A1 | 9/2004 | Babashan |
| 2007/0208233 | A1 | 9/2007 | Kovacs |
| 2008/0001735 | A1 | 1/2008 | Tran |
| 2008/0125288 | A1 | 5/2008 | Case |
| 2008/0218310 | A1 | 9/2008 | Alten et al. |
| 2009/0030333 | A1 | 1/2009 | McDonough |
| 2009/0069702 | A1 | 3/2009 | How et al. |
| 2009/0112072 | A1 | 4/2009 | Banet et al. |
| 2009/0192823 | A1 | 7/2009 | Hawkins et al. |
| 2010/0280331 | A1 | 11/2010 | Kaufman et al. |
| 2010/0292050 | A1 | 11/2010 | DiBenedetto et al. |
| 2010/0292599 | A1 | 11/2010 | Oleson et al. |
| 2011/0062237 | A1 | 3/2011 | Chaves |
| 2012/0146784 | A1 | 6/2012 | Hines et al. |
| 2012/0235821 | A1 | 9/2012 | Dibenedetto et al. |
| 2012/0246795 | A1 | 10/2012 | Scheffler et al. |
| 2012/0306643 | A1 | 12/2012 | Dugan |
| 2013/0120106 | A1 | 5/2013 | Cauwels et al. |
| 2013/0175334 | A1 | 7/2013 | Miller |
| 2013/0231711 | A1 | 9/2013 | Kaib |
| 2014/0040626 | A1 | 2/2014 | Fredinburg et al. |
| 2014/0125619 | A1 | 5/2014 | Panther et al. |
| 2014/0135644 | A1 | 5/2014 | Kim |
| 2014/0221855 | A1 | 8/2014 | McCaffrey |
| 2014/0228649 | A1 | 8/2014 | Rayner et al. |
| 2014/0275876 | A1 | 9/2014 | Hansen et al. |
| 2014/0288436 | A1 | 9/2014 | Venkatraman et al. |
| 2014/0318699 | A1 | 10/2014 | Longinotti-Buitoni et al. |
| 2014/0323827 | A1 | 10/2014 | Ahmed et al. |
| 2015/0061889 | A1 | 3/2015 | Kotaki et al. |
| 2015/0061891 | A1 | 3/2015 | Oleson et al. |
| 2015/0081169 | A1 | 3/2015 | Pisz |
| 2015/0088002 | A1 | 3/2015 | Podhajsky et al. |
| 2015/0099991 | A1 | 4/2015 | Yamaguchi et al. |
| 2015/0182841 | A1 | 7/2015 | Martikka et al. |
| 2015/0230752 | A1 | 8/2015 | Fort |
| 2015/0231481 | A1 | 8/2015 | Jones et al. |
| 2015/0286285 | A1* | 10/2015 | Pantelopoulos ........ G06F 3/048 345/156 |
| 2015/0305674 | A1 | 10/2015 | McPherson et al. |
| 2016/0058313 | A1 | 3/2016 | Sato |
| 2016/0098581 | A1 | 4/2016 | Ascencio et al. |
| 2016/0120460 | A1 | 5/2016 | Eom |
| 2016/0134642 | A1 | 5/2016 | Hamid et al. |
| 2016/0135516 | A1 | 5/2016 | Cobbett et al. |
| 2016/0159106 | A1 | 6/2016 | De Castro |
| 2016/0192716 | A1 | 7/2016 | Lee |
| 2016/0256104 | A1 | 9/2016 | Romem et al. |
| 2016/0371438 | A1 | 12/2016 | Annulis |
| 2016/0374588 | A1 | 12/2016 | Shariff et al. |
| 2017/0031435 | A1 | 2/2017 | Raffle et al. |
| 2017/0071548 | A1 | 3/2017 | Wiebe et al. |
| 2017/0086519 | A1 | 3/2017 | Vigano' et al. |
| 2017/0094216 | A1 | 3/2017 | Ekambaram et al. |
| 2017/0140120 | A1 | 5/2017 | Thrower |
| 2017/0181703 | A1 | 6/2017 | Kaib et al. |
| 2017/0196513 | A1 | 7/2017 | Longinotti-Buitoni et al. |
| 2017/0243615 | A1 | 8/2017 | Tabak |
| 2017/0303864 | A1 | 10/2017 | Su |
| 2017/0332946 | A1 | 11/2017 | Kikkeri |
| 2017/0368413 | A1 | 12/2017 | Shavit |
| 2018/0092698 | A1 | 4/2018 | Chopra et al. |
| 2018/0174683 | A1 | 6/2018 | Franz et al. |
| 2018/0228406 | A1 | 8/2018 | Mendelsohn |
| 2018/0232925 | A1 | 8/2018 | Frakes et al. |
| 2018/0300919 | A1 | 10/2018 | Muhsin et al. |
| 2018/0345079 | A1 | 12/2018 | Lindman et al. |
| 2018/0353152 | A1 | 12/2018 | Teji |
| 2018/0358119 | A1 | 12/2018 | Bhushan et al. |
| 2019/0000384 | A1 | 1/2019 | Gupta et al. |
| 2019/0037932 | A1 | 2/2019 | Martin et al. |
| 2019/0053469 | A1 | 2/2019 | Mardirossian |
| 2019/0090765 | A1 | 3/2019 | Cuccinello |
| 2019/0196411 | A1 | 6/2019 | Yuen |
| 2019/0246734 | A1 | 8/2019 | Nurse et al. |
| 2019/0261888 | A1* | 8/2019 | Zdeblick ............ A61B 5/02416 |
| 2020/0333837 | A1 | 10/2020 | Weiner |
| 2020/0367758 | A1 | 11/2020 | Kimura et al. |
| 2021/0076756 | A1* | 3/2021 | Williams ............. A41D 13/012 |
| 2021/0178063 | A1* | 6/2021 | Parikh .................... G06V 40/23 |
| 2022/0101994 | A1 | 3/2022 | Crofts et al. |
| 2022/0142572 | A1 | 5/2022 | Crofts et al. |
| 2023/0115286 | A1 | 4/2023 | Crofts et al. |

FOREIGN PATENT DOCUMENTS

| | | |
|---|---|---|
| CN | 208624750 U | 3/2019 |
| CN | 110584627 A | 12/2019 |
| CN | 209928492 U | 1/2020 |
| CN | 111035376 A | 4/2020 |
| EP | 3332698 A1 | 6/2018 |
| EP | 3431146 A1 | 1/2019 |
| GB | 2476690 A | 7/2011 |
| GB | 2561575 A | 10/2018 |
| GB | 2563065 A | 12/2018 |
| GB | 2565330 A | 2/2019 |
| GB | 2567533 A | 4/2019 |
| GB | 2586950 A | 3/2021 |
| GB | 2590985 A | 7/2021 |
| GB | 2590986 A | 7/2021 |
| GB | 2591819 A | 8/2021 |
| GB | 2593433 A | 9/2021 |
| GB | 2593434 A | 9/2021 |
| GB | 2596157 A | 12/2021 |
| GB | 2596158 A | 12/2021 |
| GB | 2596782 A | 1/2022 |
| GB | 2596783 A | 1/2022 |
| JP | 2015-073807 A | 4/2015 |
| KR | 10-1907383 B1 | 10/2018 |
| WO | 00/04522 A1 | 1/2000 |
| WO | 2006/009830 A2 | 1/2006 |
| WO | 2008/038141 A2 | 4/2008 |
| WO | 2012/167026 A2 | 12/2012 |
| WO | 2014/192002 A1 | 12/2014 |
| WO | 2015/056262 A1 | 4/2015 |
| WO | 2017/198978 A1 | 11/2017 |
| WO | 2018/134432 A1 | 7/2018 |
| WO | 2018/145719 A1 | 8/2018 |
| WO | 2018/152475 A1 | 8/2018 |
| WO | 2019/086908 A1 | 5/2019 |
| WO | 2019/104374 A1 | 6/2019 |
| WO | WO 2019223919 | 11/2019 |

OTHER PUBLICATIONS

U.S. Appl. No. 17/432,583, filed Aug. 20, 2021, Adam Lee Edward Crofts.
U.S. Appl. No. 18/081,016, filed Dec. 14, 2022, Adam Lee Edward Crofts.
U.S. Appl. No. 17/796,845, filed Aug. 1, 2022, Michael John Lynch.
U.S. Appl. No. 17/999,972, filed Nov. 28, 2022, Michael John Lynch.
"EMGlare Heart" emglare.com, [online] available from https://emplare.com/.
Enflux Exercise Clothing: Improve Form! Real-time Analysis, https://www.kickstarter.com/projects/1850884998/enflux-smart-

(56) References Cited

OTHER PUBLICATIONS clothing-3d-workout-tracking-and-form/description, Mar. 1, 2017, Publisher: Enflux exercise clothing, ickstarter.com, [online].
Examination Report received in GB1908181.9 mailed Apr. 16, 2021.
Examination Report received in GB1908181.9 mailed Mar. 16, 2020.
Examination Report received in GB1908187.6 mailed May 29, 2020.
GB Combined Search Report and Examination Report dated Dec. 12, 2019 of GB Application 1908187.6.
GB Search Report dated Dec. 9, 2019 of GB Application 1908181.9.
International Search Report and Written Opinion of PCT/GB2020/051361 dated Aug. 4, 2020.
International Search Report and Written Opinion received for PCT Patent Application No. PCT/GB2021/050284, mailed on Apr. 12, 2021, 13 pages.
International Search Report and Written Opinion received for PCT Patent Application No. PCT/GB2021/051489, mailed on Sep. 20, 2021, 11 pages.
International Search Report received in PCT/GB2020/051360 mailed Aug. 20, 2020.
Lightbody et al., A versatile high-performance visual fiducial marker detection system with scalable identity encoding, Apr. 3, 2017, pp. 276-282, Publisher: Proceedings of the Symposium on Applied Computing.
Naked Labs (https://nakedlabs.com/naked-home-body-scanner, available at least from Oct. 4, 2018, 2 pages) (Year: 2018).
Peter Lightbody et al: "A versatile high-performance visual fiducial marker detection system with scalable identity encoding", Applied Computing, ACM, 2 Penn Plaza, Suite 701 New York NY 10121-0701 USA, Apr. 3, 2017 pp. 276-282, XP058337320.
Written Opinion received in PCT/GB2020/051360 mailed Aug. 20, 2020.
YouTube Video, titled "QR Code & Bluetooth Connection Tutorial with Shimmer", purportedly uploaded by "Shimmer Sensing" on Feb. 6, 2014, available from https://www.youtube.com/watch?v=l6pZLr2h9ag Screenshot provided (taken on Aug. 13, 2021).
GB Combined Search Report and Examination Report of GB Application 2001804.0 dated Aug. 21, 2020.
International Search Report and Written Opinion of PCT/GB2021/050285 dated Apr. 30, 2021.

\* cited by examiner

WEARABLE ARTICLE

CROSS-REFERENCE TO RELATED APPLICATIONS

This application is a national stage application under 35 U.S.C. § 371 of International Application PCT/GB2021/050285, filed Feb. 9, 2021, which claims priority of GB Patent Application 2001804.0, filed Feb. 10, 2020. The disclosures of which are hereby incorporated by reference herein in their entireties.

The present invention is directed towards a wearable article, and in particular a wearable article arranged to retain an electronics module.

BACKGROUND

US 20160209016 A1 discloses a control module supported within a jacket. The control module is located within a pocket. The control module has an activation button which covers at least 40% of the surface area of the control module. A visual indicator is pressed on the jacket at a position in front of the activation button on the control module. The visual indicator has a size smaller than the activation button so that a significant portion of the activation button is located adjacent to the visual indicator even if the control module moves with respect to the visual indicator. Pushing on the visual indicator pushes on the larger activation button and activates or deactivates the control module.

It is desirable to provide a system which overcomes at least some of the problems associated with the prior art, whether explicitly discussed herein or otherwise.

SUMMARY

According to the present disclosure there is provided a wearable article as set forth in the appended claims. Other features of the invention will be apparent from the dependent claims, and the description which follows.

According to a first aspect of the disclosure, there is provided a wearable article. The wearable article comprises an electronics module holder arranged to hold an electronics module. The wearable article comprises a visual marker located on an outside surface of the wearable article. The visual marker is located at a position corresponding to the electronics module holder. The wearable article further comprises an electronics module. The electronics module comprises a housing; a processor disposed within the housing; and an electronics component disposed within the housing. The electronics component is arranged to detect an object being brought into proximity with the electronics module. The visual marker is configured to indicate the location of the electronics component of the electronics module when positioned in the electronics module holder such that an object being brought into the vicinity of the visual marker is detectable by the electronics component of the electronics module. The electronics component is arranged to generate a signal in response to the object being brought into the vicinity of the visual marker. The processor is arranged to receive the signal generated by the electronics component and is arranged to perform an action in response to receiving the signal.

Advantageously, the wearable article provides an electronics module with an electronics component disposed within the housing of the electronics module. The electronics component is arranged to detect an object being brought into proximity with the electronics module. The electronics component enables the electronics module to be controlled from an outside surface of the wearable article when the electronics module is positioned within the electronics module holder. This means that when the electronics module is positioned within the wearable article and covered by one or more layers of the wearable article, the electronics module may be still be controlled by a user from the outside surface of the wearable. Effective control of the electronics module is provided without requiring the electronics module to be removed from its holder in the wearable article.

As a further benefit, the electronics component is provided inside the housing and therefore is not an activation button extending from an outer surface of the housing. Beneficially, this means that a large activation button occupying at least 40% of the surface of the electronics module is not required. An activation button on the outside surface of the housing increases the overall thickness of the electronics module as the button is required to move along the longitudinal axis of the housing. Moreover, it can be challenging to manipulate a button from an outside surface of the wearable article. This is particularly the case if the wearable article comprises one or more thick layers of fabric.

The electronics component may comprise a sensor.

The sensor may comprise a proximity sensor. The proximity sensor may comprise an antenna. The antenna may be arranged such that a current is induced in the antenna in response to an object being brought into the vicinity of the visual marker. The object may be a mobile device comprising an antenna arranged to induce a current in the antenna of the electronics component.

The sensor may comprise a motion sensor. The electronics component may be arranged to generate a signal in response to detecting an object being brought into contact with the outside surface of the wearable article in the vicinity of the visual marker. The motion sensor may comprise an accelerometer.

The electronics module may further comprise a communicator connected to the processor. The processor may be configured to activate, in response to receiving the signal, the communicator to transmit and/or receive data. The communicator may be arranged to transmit data to and/or receive data from the object.

The communicator may comprise a short-range communicator configured to communicate using a short-range communication protocol. The short-range communicator may be arranged to transmit and/or receive data over a communication range of up to 50 metres, optionally up to 30 metres, optionally up to 10 metres, and optionally up to 1 metre. The short-range communicator may comprise one or more of a near field communication, NFC, wireless body area network, BAN, and a wireless personal area network, PAN, communication antenna. The short-range communicator may comprise one or more of a NFC, Bluetooth®, Bluetooth® Low Energy, Bluetooth® Mesh, Bluetooth® 5, Thread, Zigbee, IEEE 802.15.4, and Ant communicator.

The communicator may comprise a medium-range communicator. The medium-range communicator may be arranged to transmit and/or receive data over a communication range of up to 200 metres, optionally up to 100 metres, optionally up to 50 metres, optionally up to 30 metres. The medium-range communicator may comprise one or more of a wireless near-me area network, NAN, a wireless local area network, WLAN, and a Wi-Fi communication antenna.

The first antenna may comprise a long-range communicator. The long-range communicator may be arranged to transmit and/or receive data over a communication range of over 200 metres, optionally over 100 metres, optionally over 50 metres. The long-range communicator may comprise one or more of a wireless metro-area network, WMAN, a wireless wide area network, WAN, a low power wide area network, LWAN, and a cellular antenna. The cellular antenna may be configured to transmit or receive data over one or more of a fourth generation (4G) LTE, LTE Advanced (LTE-A), LTE Cat-M1, LTE Cat-M2, NB-IoT, fifth generation (5G), sixth generation (6G), and/or any other present or future developed cellular wireless network.

The communicator may comprise an antenna. The antenna may be arranged such that a current is induced in the antenna in response to an object being brought into the vicinity of the visual marker.

The communicator may be a first communicator. The electronics module may further comprise a second communicator connected to the processor. The processor may be configured to activate the second communicator to transmit and/or receive data. The first communicator and the second communicator may any combination of a short-range communicator, medium-range communicator, and long-range communicator. The first communicator and the second communicator may both be short-range communicators. The first communicator may comprise a near field communication (NFC) circuit configured to communicate using an NFC communications protocol. The second communicator may comprise a Bluetooth® communication circuit configured to communicate using a Bluetooth® communications protocol.

The electronics module holder may be provided on the inside surface of the wearable article. That is, the electronics module holder may be located within the wearable article.

The electronics module holder may be provided on the outside surface of the wearable article. The electronics module holder may have an outer fabric layer that covers the electronics module when positioned in the electronics module holder.

The electronics module holder may be a pocket. The pocket may be an internal pocket or an external pocket.

The electronics module holder may be provided with a surface which increases friction between the inner surface and the electronics module when positioned within the electronics module holder.

The electronics module may be provided with a surface which increases friction between the inner surface of the electronics module holder and the electronics module when positioned within the electronics module holder.

The visual marker may comprise a machine-readable code. The machine-readable code may be a QR code.

The electronics module may further comprise a light source arranged to emit light.

The wearable article may be constructed such that light emitted by the light source is visible from the outside surface of the wearable article.

The wearable article may comprise an opening positioned such that light emitted by the light source is visible from the outside surface of the wearable article. The wearable article may comprise a window constructed from a transparent, translucent, or light-diffracting material such that light emitted by the light source is visible from the outside surface of the wearable article.

The signals may relate to the activity of a user wearing the wearable article. The processor may be configured to process the signals so as to determine whether the activity of the user is within a predetermined allowable range.

The light source may be configured to emit light based on the determination by the processor, wherein the emitted light is for indicating to the user whether the activity of the user is within the predetermined allowable range.

The wearable article may be a garment.

The signal generated by the electronics component may be a signal for changing the operational mode of the electronics module. The signal may be used to cause the processor or other components of the electronics module to wake-up from a low-power mode. The signal may be used to cause the processor to transmit data or change the type of data transmitted. The signal may cause the processor to perform any form of controlling operation.

The electronics module may be arranged to interface with a sensing component of the wearable article. The sensing component may be a biosensing component arranged to measure a biosignal. The electronics module may further comprise an interface element arranged to communicatively couple with the sensing component of the wearable article so as to receive signals from the wearable article.

The wearable article may comprise one or more sensing components. The sensing components may be biosensing components. The sensing components may comprise one or more components of a temperature sensor, a humidity sensor, a motion sensor, an electropotential sensor, an electroimpedance sensor, an optical sensor, an acoustic sensor. Here, "component" means that not all of the components of the sensor may be provided in the wearable article. The processing logic, power and other functionality may be provided in the electronics module. The wearable article may only comprise the minimal functionality to perform the sensing such as by only including sensing electrodes. The temperature sensor may be arranged to measure an ambient temperature, a skin temperature of a human or animal body, or a core temperature of a human or animal body. The humidity sensor may be arranged to measure humidity or skin-surface moisture levels for a human or animal body. The motion sensor may comprise one or more of an accelerometer, a gyroscope, and a magnetometer sensor. The motion sensor may comprise an inertial measurement unit. The electropotential sensor may be arranged to perform one or more bioelectrical measurements. The electropotential sensor may comprise one or more of electrocardiography (ECG) sensor modules, electrogastrography (EGG) sensor modules, electroencephalography (EEG) sensor modules, and electromyography (EMG) sensor modules. The electroimpedance sensor may be arranged to perform one or more bioimpedance measurements. Bioimpedance sensors can include one or more of plethysmography sensor modules (e.g., for respiration), body composition sensor modules (e.g., hydration, fat, etc.), and electroimpedance tomography (EIT) sensors. An optical sensor may comprise a photoplethysmography (PPG) sensor module or an orthopantomogram (OPG) sensor module.

According to a second aspect of the disclosure, there is provided a wearable article. The wearable article comprises an electronics arrangement. The electronics arrangement comprises a processor; and an electronics component. The electronics component comprises one or more of a proximity sensor and a motion sensor. The one or more of the proximity sensor and the motion sensor is arranged to detect an object being brought into proximity with the electronics component. The wearable article further comprises a visual marker located on an outside surface of the wearable article. The visual marker is located at a position corresponding to the electronics component. The visual marker is configured to indicate the location of the electronics component such that an object being brought into the vicinity of the visual marker is detectable by the electronics component. The electronics component is arranged to generate a signal in response to the object being brought into the vicinity of the visual marker. The processor is arranged to receive the signal generated by the electronics component and is arranged to perform an action in response to receiving the signal.

The wearable article may comprise any or all of the features of the wearable article of the first aspect of the disclosure.

According to a third aspect of the disclosure, there is provided a wearable article. The wearable article comprises an electronics arrangement. The electronics arrangement comprises: a biosensing component arranged to measure biosignals from a user wearing the garment; a processor arranged to process the biosignals received from the sensing component; and an electronics component arranged to detect an object being brought into proximity with the electronics component. The wearable article further comprises a visual marker located on an outside surface of the wearable article. The visual marker is located at a position corresponding to the electronics component. The visual marker is configured to indicate the location of the electronics component such that an object being brought into the vicinity of the visual marker is detectable by the electronics component. The electronics component is arranged to generate a signal in response to the object being brought into the vicinity of the visual marker. The processor is arranged to receive the signal generated by the electronics component and is arranged to perform an action in response to receiving the signal.

The wearable article may comprise any or all of the features of the wearable article of the first aspect of the disclosure.

According to a fourth aspect of the disclosure, there is provided a wearable article. The wearable article comprises a biosensing component arranged to measure biosignals from a user wearing the garment. The wearable article comprises an electronics module holder arranged to hold an electronics module; and a visual marker located on an outside surface of the wearable article, the visual marker being located at a position corresponding to the electronics module holder. The wearable article further comprises an electronics module. The electronics module comprises a processor arranged to process biosignals received from the biosensing component of the wearable article; and an electronics component arranged to detect an object being brought into proximity with the electronics module. The visual marker is configured to indicate the location of the electronics component of the electronics module when positioned in the electronics module holder such that an object being brought into the vicinity of the visual marker is detectable by the electronics component of the electronics module. The electronics component is arranged to generate a signal in response to the object being brought into the vicinity of the visual marker. The processor is arranged to receive the signal generated by the electronics component and is arranged to perform an action in response to receiving the signal.

The wearable article may comprise any or all of the features of the wearable article of the first aspect of the disclosure.

The present disclosure is not limited to wearable articles. The electronics arrangement disclosed herein may be incorporated into other forms of devices such as user electronic devices (e.g. mobile phones). In additions, they may be incorporated into any form of textile article. Textile articles may include upholstery, such as upholstery that may be positioned on pieces of furniture, vehicle seating, as wall or ceiling décor, among other examples.

BRIEF DESCRIPTION OF THE DRAWINGS

Examples of the present disclosure will now be described with reference to the accompanying drawings, in which.

DETAILED DESCRIPTION

Figure 1:
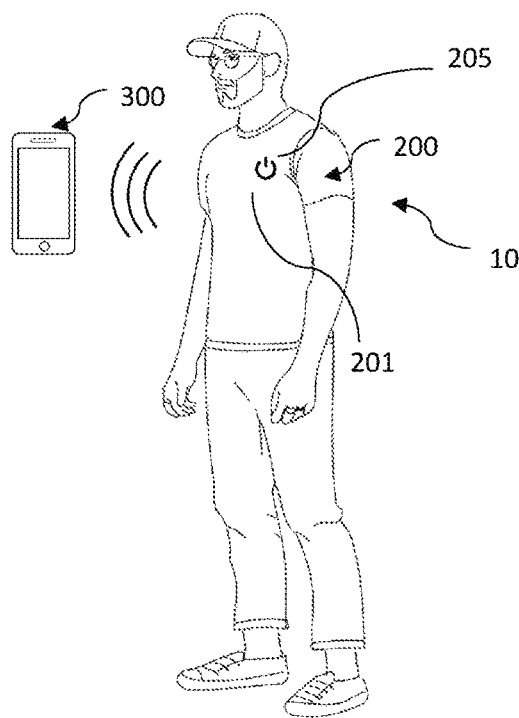
FIG. 1 shows an example system according to aspects of the present disclosure.

The following description with reference to the accompanying drawings is provided to assist in a comprehensive understanding of various embodiments of the disclosure as defined by the claims and their equivalents. It includes various specific details to assist in that understanding but these are to be regarded as merely exemplary. Accordingly, those of ordinary skill in the art will recognize that various changes and modifications of the various embodiments described herein can be made without departing from the scope and spirit of the disclosure. In addition, descriptions of well-known functions and constructions may be omitted for clarity and conciseness.

The terms and words used in the following description and claims are not limited to the bibliographical meanings, but, are merely used by the inventor to enable a clear and consistent understanding of the disclosure. Accordingly, it should be apparent to those skilled in the art that the following description of various embodiments of the disclosure is provided for illustration purpose only and not for the purpose of limiting the disclosure as defined by the appended claims and their equivalents.

It is to be understood that the singular forms "a," "an," and "the" include plural referents unless the context clearly dictates otherwise.

"Wearable article" as referred to throughout the present disclosure may refer to any form of electronic device which may be worn by a user such as a smart watch, necklace, bracelet, or glasses. The wearable article may be a textile article. The wearable article may be a garment. The garment may refer to an item of clothing or apparel. The garment may be a top. The top may be a shirt, t-shirt, blouse, sweater, jacket/coat, or vest. The garment may be a dress, brassiere, shorts, pants, arm or leg sleeve, vest, jacket/coat, glove, armband, underwear, headband, hat/cap, collar, wristband, stocking, sock, or shoe, athletic clothing, swimwear, wetsuit or drysuit. The wearable article/garment may be constructed from a woven or a non-woven material. The wearable article/garment may be constructed from natural fibres, synthetic fibres, or a natural fibre blended with one or more other materials which can be natural or synthetic. The yarn may be cotton. The cotton may be blended with polyester and/or viscose and/or polyamide according to the particular application. Silk may also be used as the natural fibre. Cellulose, wool, hemp and jute are also natural fibres that may be used in the wearable article/garment. Polyester, polycotton, nylon and viscose are synthetic fibres that may be used in the wearable article/garment. The garment may be a tight-fitting garment. Beneficially, a tight-fitting garment helps ensure that the sensor devices of the garment are held in contact with or in the proximity of a skin surface of the wearer. The garment may be a compression garment. The garment may be an athletic garment such as an elastomeric athletic garment.

The following description refers to particular examples of the present disclosure where the wearable article is a garment. It will be appreciated that the present disclosure is not limited to garments and other forms of wearable article are within the scope of the present disclosure as outlined above.

Referring to FIG. 1, there is shown an example system 10 according to aspects of the present disclosure. The system 10 comprises electronics module 100 (FIG. 2), and a garment 200. The system 10 further comprises a mobile device 300. The garment 200 is worn by a user. The electronics module 100 is attached to the garment 200. The electronics module 100 is provided within the garment 200 and is not visible in FIG. 1.

The electronics module 100 is arranged to integrate with sensing components incorporated into the garment 200 so as to obtain signals from the sensing components. The combination of the electronics module 100 and the sensing components of the garment 200 can be considered as an electronics arrangement according to aspects of the present disclosure. The components of the electronics module 100 can be considered as an electronics arrangement according to aspect of the present disclosure. The electronics arrangement may be distributed components and may not be all contained within a housing. The following description refers to particular examples of the present disclosure where the electronics arrangement comprises an electronics module with a housing. will be appreciated that the present disclosure is not limited to electronics modules comprising housings and other forms of electronics arrangements are within the scope of the present disclosure as outlined above. The electronics module 100 may be a standalone device such as a portable electronics device, e.g. a mobile phone.

The sensing components may comprise components of sensors. The sensing components may comprise electrodes. The electronics module 100 is further arranged to wirelessly communicate data to the mobile device 300. Various protocols enable wireless communication between the electronics module 100 and the mobile device 300. Example communication protocols include Bluetooth®, Bluetooth® Low Energy, and near-field communication (NFC).

The electronics module 100 may be removable from the garment 200. The mechanical coupling of the electronic module 100 to the garment 200 may be provided by a mechanical interface such as a clip, a plug and socket arrangement, etc. The mechanical coupling or mechanical interface may be configured to maintain the electronic module 100 in a particular orientation with respect to the garment 200 when the electronic module 100 is coupled to the garment 200. This may be beneficial in ensuring that the electronic module 100 is securely held in place with respect to the garment 200 and/or that any electronic coupling of the electronic module 100 and the garment 200 (or a component of the garment 200) can be optimized. The mechanical coupling may be maintained using friction or using a positively engaging mechanism, for example.

Beneficially, the removable electronic module 100 may contain all of the components required for data transmission and processing such that the garment 200 only comprises the sensor components and communication pathways. In this way, manufacture of the garment 200 may be simplified. In addition, it may be easier to clean a garment 200 which has fewer electronic components attached thereto or incorporated therein. Furthermore, the removable electronic module 100 may be easier to maintain and/or troubleshoot than embedded electronics. The electronic module 100 may comprise flexible electronics such as a flexible printed circuit (FPC). The electronic module 100 may be configured to be electrically coupled to the garment 200.

It may be desirable to avoid direct contact of the electronic module 100 with the wearer's skin while the garment 200 is being worn. It may be desirable to avoid the electronic module 100 coming into contact with sweat or moisture on the wearer's skin. The electronic module 100 may be provided with a waterproof coating or waterproof casing. For example, the electronic module 100 may be provided with a silicone casing. It may further be desirable to provide an electronics module holder such as a pocket in the garment to contain the electronic module in order to prevent chafing or rubbing and thereby improve comfort for the wearer. The pocket may be provided with a waterproof lining in order to prevent the electronic module 100 from coming into contact with moisture.

The garment 200 comprises a visual marker 205 located on the outside surface of the garment 200.

Figure 2:
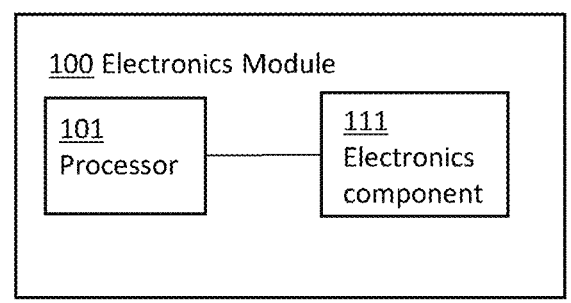
FIG. 2 shows a schematic diagram for an example electronics module according to aspects of the present disclosure.

Referring to FIG. 2, there is shown a simplified schematic diagram of an example electronics module 100 according to aspects of the present disclosure. The electronics module 100 comprises a housing. The electronics module 100 comprises a processor 101 disposed within the housing. The processor 101 is configured to process signals sensed by a sensing component of the electronics module 100 and/or the garment 200. The electronics module 100 comprises an electronics component 111 disposed within the housing. The electronics component 111 is arranged to detect an object being brought into vicinity with the electronics module 100.

Referring to FIGS. 1 and 2, when the electronics module 100 is disposed within the electronics module holder of the garment 200, the electronics module 100 is not easily visible from the outside of the garment 200 and may even be hidden within the garment 200. This is particularly the case when the garment 200 comprises padding in the vicinity of the electronics module holder to disguise the visual appearance of the electronics module 100. The visual marker 205 on the outside surface of the garment 200 indicates the location of the electronics component 111 of the electronics module 100 positioned in the electronics module holder. In this way, when an object is brought into the vicinity of the visual marker 205, the object is detectable by the electronics component 111 of the electronics module 100. The object may be the mobile device 300 or a part of the user's body such as the user's hand. The electronics component 111 is arranged to generate a signal in response to the object being brought into the vicinity of the visual marker 205. The processor 101 is arranged to receive the signal generated by the electronics component 111 and is arranged to perform an action in response to receiving the signal. In this way, operation of the processor 101 of the electronics module 100 is controlled based on the electronics component 111 detecting an object being brought into its vicinity.

The signal generated by the electronics component 111 may trigger the processor 101 to transition from a low power mode to a normal power mode. Beneficially, prior to the electronics component 111 detecting an object being brought into proximity with the electronics module 100, the processor and other elements of the electronics module 100 may be operating in a low power mode. This may mean that they are not supplied with power or only supplied with a minimal amount of power such as for refreshing an internal memory. This reduces unnecessary power consumption for the electronics module 100. Once the object is brought into proximity with the electronics module 100, the electronics component 111 may cause the processor 101 to wake-up. In an example implementation, when the electronics component 111 detects an object being brought into proximity with the electronics module 100, the electronics component 111 sends an interrupt signal to the processor 101. This causes the processor 101 to wake-up. Additionally or separately, the signal generated by the electronics component 111 may cause the processor 101 to wake-up other components of the electronics module 100, control other components of the electronics module 100 to perform an action such as transmit data, or change an operational mode of the processor 101. It will be appreciated that any number of control operations may be performed by the processor 101 in response to receiving the signal from the electronics component 111.

Figure 3:
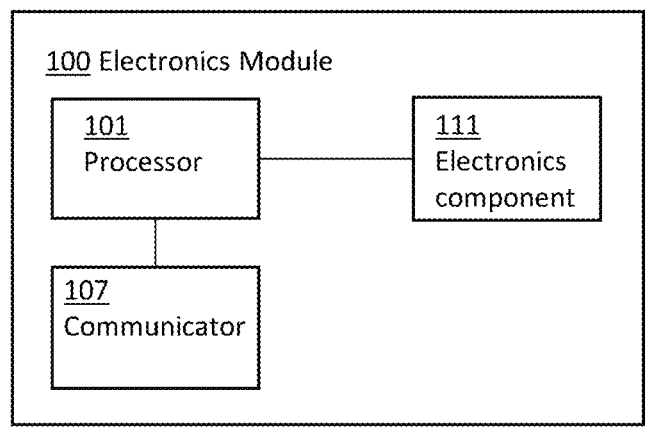
FIG. 3 shows a schematic diagram for another example electronics module according to aspects of the present disclosure.

Referring to FIG. 3, there is shown another example of electronics module 100 according to aspects of the present disclosure. The electronics module 100 comprises the processor 101 and electronics component 111 of FIG. 2. The electronics module 100 further comprises a communicator 107. The communicator 107 is connected to the processor 101. The processor 101 is configured to activate, in response to receiving the signal from the electronics component 111, the communicator 107 to transmit and/or receive data. The communicator 107 may be arranged to transmit data to and/or receive data from the object. In this way, tapping the object against the visual symbol can trigger the communicator 107 to transmit the data to the object (e.g. mobile device 300). The visual marker 205 may, for example, facilitate a simple tap to pair operation.

The communicator 107 may be a mobile/cellular communicator operable to communicate the data wirelessly via one or more base stations. The communicator 107 may provide wireless communication capabilities for the garment and enables the garment to communicate via one or more wireless communication protocols such as used for communication over: a wireless wide area network (WWAN), a wireless metroarea network (WMAN), a wireless local area network (WLAN), a wireless personal area network (WPAN), Bluetooth® Low Energy, Bluetooth® Mesh, Bluetooth® 5, Thread, Zigbee, IEEE 802.15.4, Ant, a near field communication (NFC), a Global Navigation Satellite System (GNSS), a cellular communication network, or any other electromagnetic RF communication protocol. The cellular communication network may be a fourth generation (4G) LTE, LTE Advanced (LTE-A), LTE Cat-M1, LTE Cat-M2, NB-IoT, fifth generation (5G), sixth generation (6G), and/or any other present or future developed cellular wireless network. A plurality of communicators may be provided for communicating over a combination of different communication protocols.

The communicator may comprise an antenna. The antenna may be arranged such that a current is induced in the antenna in response to an object being brought into the vicinity of the visual marker.

The communicator 107 may be a first communicator 107. The electronics module 100 may further comprise a second communicator (not shown) connected to the processor 101. The processor 101 may be configured to activate the second communicator to transmit and/or receive data. In one example, the first communicator 107 comprises a near field communication (NFC) circuit configured to communicate using an NFC communications protocol, and the second communicator comprises a Bluetooth® communication circuit configured to communicate using a Bluetooth® communications protocol. The object (e.g. mobile device 300) tapping against the visual marker 205 may cause the first communicator 107 to be controlled to transmit information to the object over the first communication protocol (e.g. NFC). The information may facilitate pairing between the object and the second communicator over the second communication protocol (e.g. Bluetooth®). Of course, communicators for communicating using other communication protocols are within the scope of the present disclosure.

Figure 4:
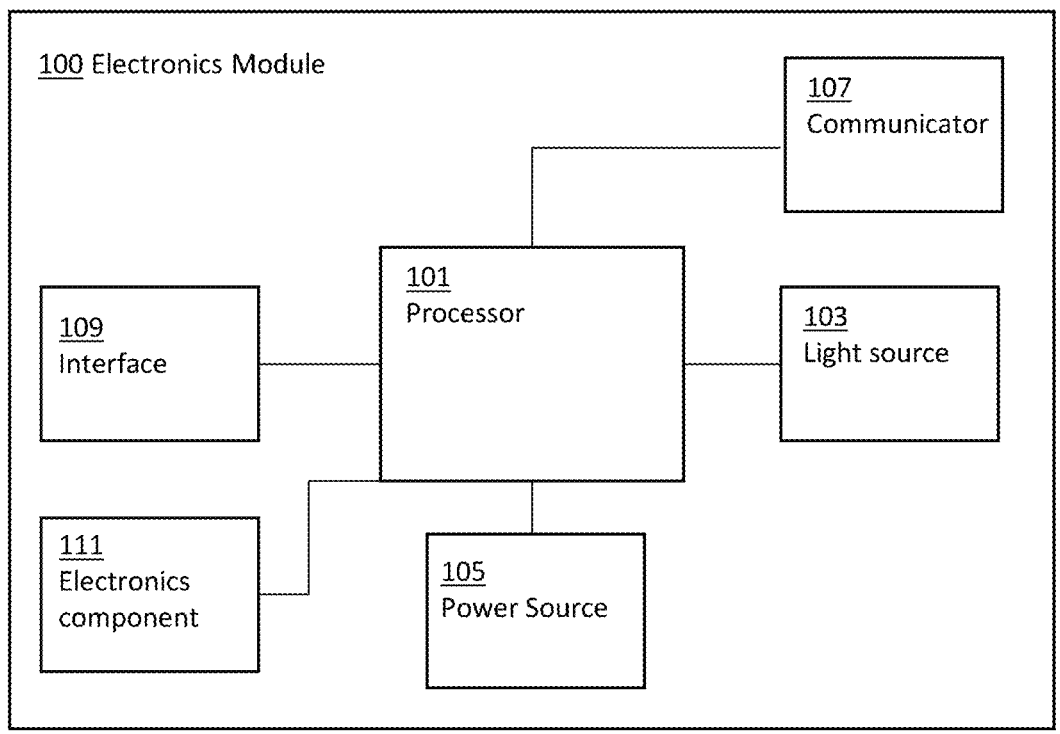
FIG. 4 shows a schematic diagram for yet another example electronics module according to aspects of the present disclosure.

Referring to FIG. 4, there is shown another example of electronics module 100 according to aspects of the present disclosure. The electronics module 100 comprises the processor 101, electronics component 111, and communicator 107 of FIG. 3.

The electronics module 100 further comprises a light source 103 controlled by the processor 101. The processor 101 is configured to process signals sensed by a sensing component of the electronics module 100 and/or the garment 200. The signals relate to the activity of a user wearing the garment 200. The processor 101 is, in some examples, configured to process the signals so as to determine whether the activity of the user is within a predetermined allowable range. The light source 103 is configured to emit light based on the determination by the processor 101. The emitted light is for indicating to the user whether the activity of the user is within the predetermined allowable range. The garment 200 is constructed such that the emitted light is visible from the outside surface 201 of the garment 200.

This example electronics module 100 additionally comprises a power source 105 and an interface 109. The electronics module 100 of the present disclosure are not limited to this particular construction and may not comprise all of these components. In addition, the electronics module 100 may comprise alternative or additional components.

The power source 105 is coupled to the processor 101 and is arranged to supply power to the processor 101. The power source 105 may comprise a plurality of power sources. The power source 105 may be a battery. The battery may be a rechargeable battery. The battery may be a rechargeable battery adapted to be charged wirelessly such as by inductive charging. The power source 105 may comprise an energy harvesting device. The energy harvesting device may be configured to generate electric power signals in response to kinetic events such as kinetic events performed by a wearer of the garment. The kinetic event could include walking, running, exercising or respiration of the wearer. The energy harvesting material may comprise a piezoelectric material which generates electricity in response to mechanical deformation of the converter. The energy harvesting device may harvest energy from body heat of a wearer of the garment.

The energy harvesting device may be a thermoelectric energy harvesting device. The power source may be a super capacitor, or an energy cell.

The electronics module 100 may additionally comprise a Universal Integrated Circuit Card (UICC) that enables the electronics module 100 to access services provided by a mobile network operator (MNO) or virtual mobile network operator (VMNO). The UICC may include at least a read-only memory (ROM) configured to store an MNO/VMNO profile that the wearable article can utilize to register and interact with an MNO/VMNO. The UICC may be in the form of a Subscriber Identity Module (SIM) card. The electronics module 100 may have a receiving section arranged to receive the SIM card. In other examples, the UICC is embedded directly into a controller of the electronics module 100. That is, the UICC may be an electronic/embedded UICC (eUICC). A eUICC is beneficial as it removes the need to store a number of MNO profiles, i.e. electronic Subscriber Identity Modules (eSIMs). Moreover, eSIMs can be remotely provisioned to electronics modules 100. The electronics module 100 may comprise a secure element that represents an embedded Universal Integrated Circuit Card (eUICC).

The interface 109 is arranged to communicatively couple with a sensing component of the garment 200 (FIG. 1) so as to receive a signal from the sensing component. The processor 101 is communicatively coupled to the interface 109 and is arranged to receive the signals from the interface 109. The interface 109 may form a conductive coupling or a wireless (e.g. inductive) communication coupling with the electronics components of the garment 200.

The electronics module 100 is mounted on a garment 200 (FIG. 1) and conductively connected to sensing components such as electrodes of the garment via electrically conductive pathways of the garment 200. In a particular example, the sensing components are electrodes used to measure electropotential signals such as electrocardiogram (ECG) signals.

The processor 101 may be a component of a controller such as a microcontroller. The controller may have an integral communicator such as a Bluetooth® antenna. The controller may have an internal memory and may also be communicatively connected to an external memory of the electronics module such as a NAND Flash memory. The memory is used to for the storage of data when no wireless connection is available between the electronics module 100 a mobile device 300 (FIG. 1). The memory may have a storage capacity of at least 1 GB and preferably at least 2 GB. The processor 101 is connected to an interface 109 via an analog-to-digital converter (ADC) fronted end and an electrostatic discharge (ESD) protection circuit. The ADC fronted end converts the raw analog signal received from sensing components of the garment 200 into a digital signal. The ADC frontend may also perform filtering operations on the received signals.

Figure 5:
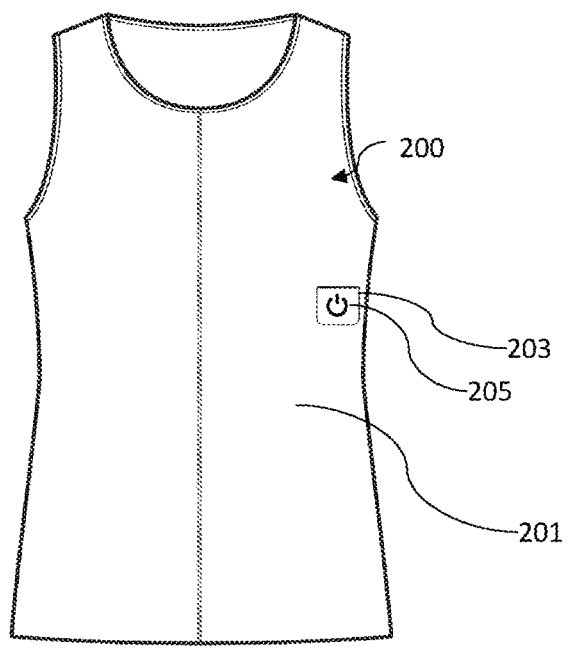
FIG. 5 shows a schematic diagram for an example wearable article according to aspects of the present disclosure.

Referring to FIG. 5, there is shown an example garment 200 according to aspects of the present disclosure. The garment 200 comprises an electronics module holder 203 provided on an outside surface 201 of the garment 200. The electronics module holder 203 is arranged to hold the electronics module according to aspects of the present disclosure. A visual symbol 205 is provided on the outside surface of the electronics module holder 203.

Figure 6:
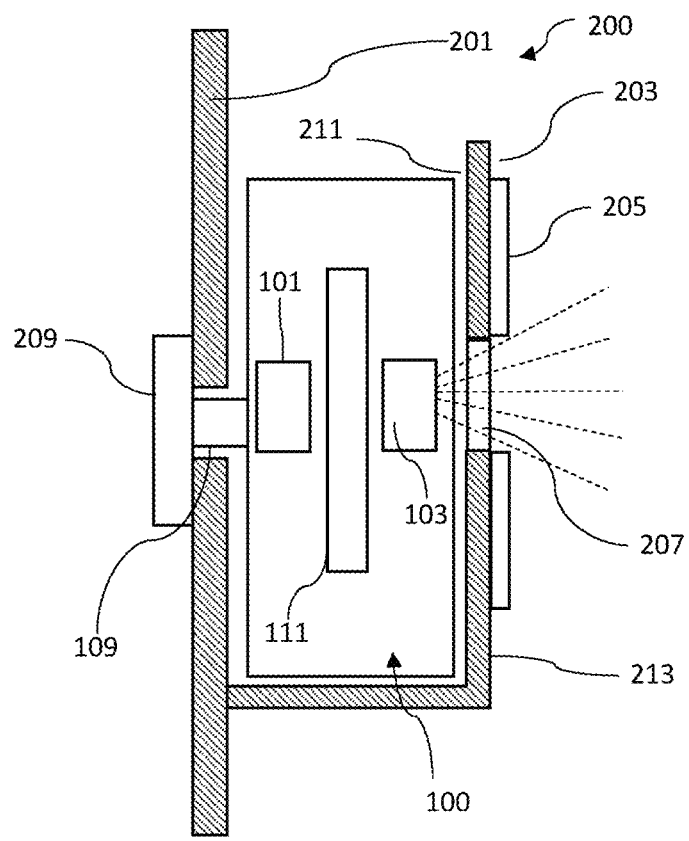
FIG. 6 shows a sectional view for an example wearable article according to aspects of the present disclosure.

Referring to FIG. 6, there is shown a sectional view of a garment 200 comprising an electronics module 100 disposed within the electronics module holder 203 of the garment 200. A terminal region 209 is provided on the inside surface of the garment 200. The terminal region 209 connects to sensing components of the garment 200 via one or more electrically conductive pathways.

The electronics module holder 203 in this example is a pocket 203 provided on the outside surface of the garment 200. The electronics module holder 203 comprises a layer of material 203 which is bonded, stitched, otherwise attached to or integrally formed with the garment 200. The electronics module holder 203 has an inner surface 211 facing the electronics module 100. The electronics module holder 203 has an outer surface 213 which can be considered as part of the outer surface 201, 213 of the garment 200.

The electronics module 100 comprises a processor 101, electronics component 111 and light source 103 according to aspects of the present disclosure. The electronics module 100 may comprise additional or separate features as described above in relation to FIGS. 2 to 4. The visual marker 205 on the outside surface of the garment 200 indicates the location of the electronics component 111 of the electronics module 100 positioned in the electronics module holder.

The garment 200 is constructed such that light emitted by the light source 103 of the electronics module 100 is visible from the outside surface of the garment 200. In this example, the garment 200 comprises an opening 207 provided in the layer of material 203 of the electronics module holder 203. The opening 207 extends from the inner surface 211 to the outer surface 213. The opening 207 is positioned such that, when the electronics module 100 is provided in the electronics module 203, the light source 103 is aligned with the opening 207. The opening 207 may be formed by removing material from the layer of material 203 of the electronics module holder 203 or the layer of material 203 may be formed to include the opening 206 during manufacture.

Rather than providing an opening 207 in the material of the garment 200, a window may instead be provided. The window may be constructed from a transparent, translucent, or light diffracting material. The use of a light diffracting material may provide a light pipe effect to help the light source 103 appear bigger than they are. In other examples, the material of the electronics module holder 203 may have an open-cell construction in the vicinity of the light source 103, when positioned in the electronics module holder 203, such that the light source 103 is visible from the outside of the garment 200.

The visual marker 205 is constructed in this example to take into account the presence of the opening 207.

Figure 7:
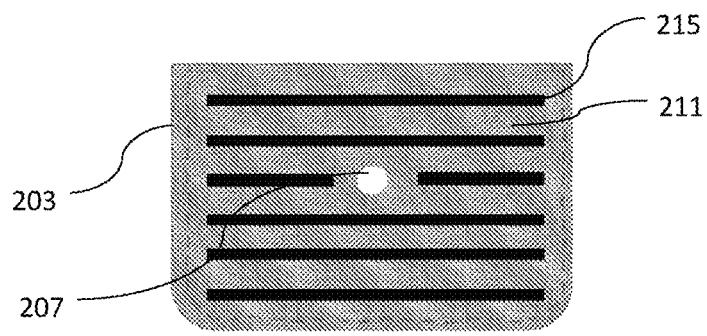
FIG. 7 shows the inner surface of an example electronics module holder of a wearable article according to aspects of the present disclosure.

Referring to FIG. 7, there is shown an example outer layer 203 of electronics module holder 203 in FIG. 6. The outer layer 203 is bonded, stitched, or otherwise attached to the garment 200. The outer layer 203 may also be integrally formed with the garment 200. FIG. 7 shows the inner surface 211 of the outer layer 203. The inner surface 211 is provided with a surface 215 which increases friction between the inner surface 211 and the electronics module 100 when positioned in the electronics module holder 203. The surface 215 comprises a number (six in this example) of horizontal lines of gripping material provided on the inner surface 211. The gripping material is a silicone-based coating. The surface 215 helps reduce unnecessary rotational or translational movement of the electronics module 100 when positioned in the electronics module holder 203 and helps maintain the interface 109 (FIG. 7) of the electronics module 100 in contact with the terminal region 209.

Figure 8:
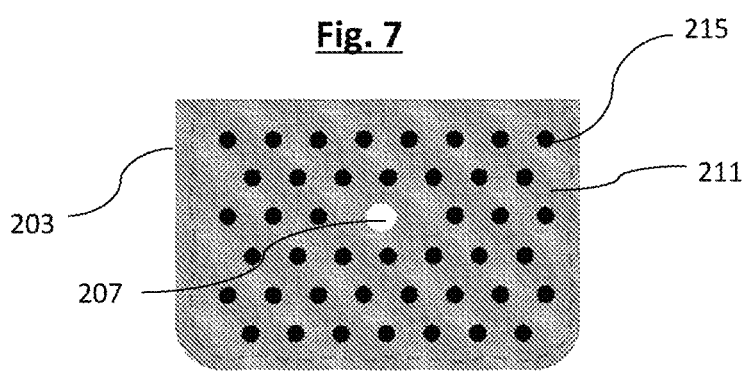
FIG. 8 shows the inner surface of another example electronics module holder of a wearable article according to aspects of the present disclosure.

Referring to FIG. 8, there is shown another example of the inner surface 211 of the electronics module holder 203. In this example, the surface 215 comprises a number of dots of gripping material provided on the inner surface 211. The gripping material is a silicone-based coating.

It will be appreciated that FIGS. 7 and 8 are only two examples of surfaces 215 used to increase friction between the electronics module holder 203 and the electronics module 100. In other examples, the electronics module 203 may be separately or additionally elasticised to help hold the electronics module 100 in place. Additionally or separately, the electronics module 100 may be provided with a surface which increases friction between the garment 200 and the electronics module 100 so as to limit motion of the electronics module 100 relative to the garment 200. The surface of the electronics module 100 may comprises a rubberised grip texture, for example.

Figure 9:
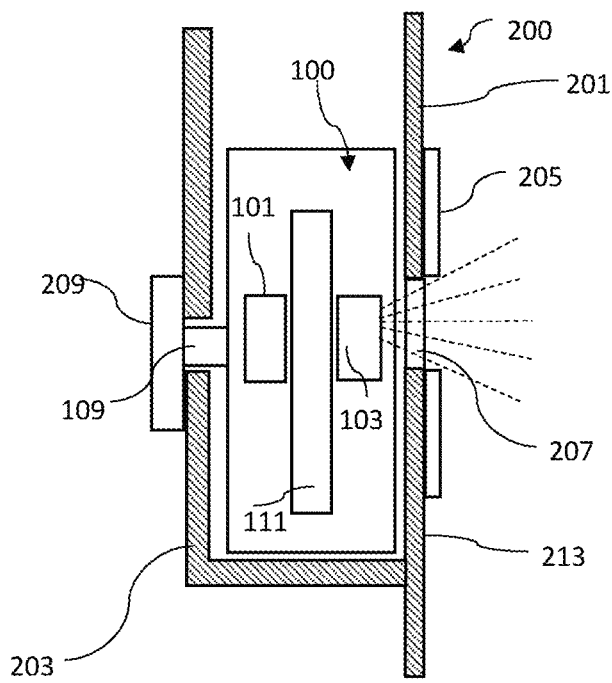
FIG. 9 shows a sectional view for another example wearable article according to aspects of the present disclosure.

Referring to FIG. 9 there is shown another example garment 200 comprising an electronics module 100 disposed within the electronics module holder 203 of the garment 200. The electronics module holder 203 in this example is a pocket 203 provided on the inside surface of the garment 200. The garment 200 is constructed such that light emitted by the light source 103 of the electronics module 100 is visible from the outside surface of the garment 200. In this example, the garment 200 comprises an opening 207 extending through the outside surface 201 of the garment 200. The opening 207 is positioned such that, when the electronics module 100 is provided in the electronics module 203, the light source 103 is aligned with the opening 207. A visual marker 205 is provided on the outside surface 201 of the garment 200. The visual marker 205 is constructed in this example to take into account the presence of the opening 207. The other features of the garment 200 may be the same as or similar to those of FIGS. 6 to 8.

In FIGS. 5 to 9, the garment 200 comprises a visual maker 205 located on the outside surface of the garment 200. The visual marker 205 is located at a position corresponding to the electronics module holder 203. The visual marker 205 indicates the location of the electronics module 100 when located in the electronics module holder 203 and in particular indicates the location of the electronics module 111.

The visual maker 205 helps a user activate and/or control the operation of the electronics module 100. When positioned in the electronics module holder 203, the electronics module 100 may be concealed or not easily visible or discernible to the user. This will particularly be the case if the garment 200 has a number of padded areas to help conceal the visual appearance of the electronics module 100 when positioned in the electronics module holder 203. Concealing the appearance of the electronics module 100 is desirable so as to make the garment 200 look more visually attractive to the user as well as fell more comfortable to wear.

Beneficially, the visual marker 205 is placed on the exterior face of the garment 200 and is visible to the user. The visual marker 205 is aligned with the electronics module 100 when positioned in the electronics module holder 203. The visual marker 205 therefore indicates the location of the electronics component 111 of the electronics module 100 when located in the electronics module holder 203.

As described previously, the electronics component 111 may be required to detect an object such as the hand of the user to approach and tap against the electronics module 100 to perform a control operation. This tapping operation may be performed on the outer surface of the garment 200 and sensed through one or more layers of fabric by the electronic component 111. The visual marker 205 in accordance with aspects of the present disclosure indicates the location of the electronic component 111 such that an object tapping on the garment 200 in the vicinity of the visual marker 205 is detectable by the input unit 111 of the electronics module 100.

Beneficially, the visual marker 205 allows the user to quickly and easily see where to tap the electronics module 100. This makes it easier for the user to control the operation of the electronics module 100 while positioned in the electronics module holder 203.

In some examples, the electronics module 100 may comprise an antenna coil such as a near field communication (NFC) coil which is used to exchange information with a mobile device 300 (FIG. 1). This may in particular be for use in tap-to-pair operations so as to pair the electronics module 100 and the mobile device 300 over another communication protocol such as Bluetooth®. The visual maker 205 can beneficially additionally or separately indicate the location of the antenna coil. This enables the user to quickly and easily see where to tap their mobile device 300 so as to enable the data exchange to take place.

Figure 10:
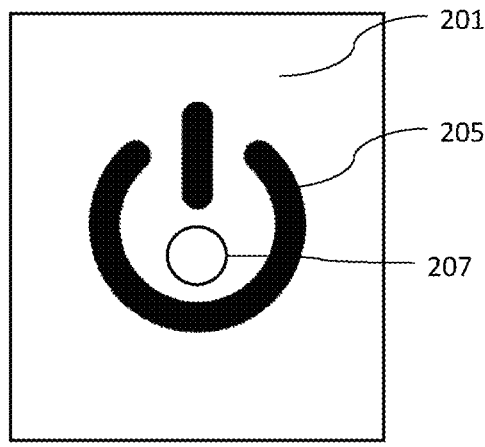
FIGS. 10 to 13 show examples of different visual markers according to aspects of the present disclosure.
Figure 11:
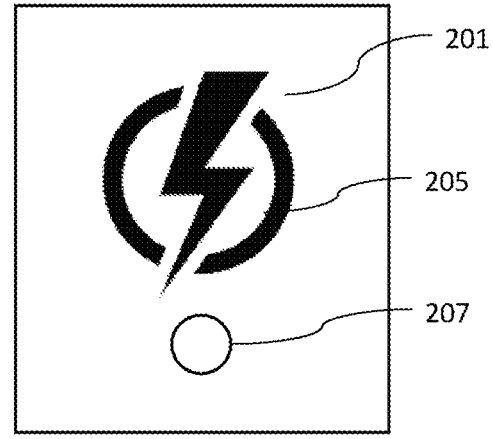
Figure 12:
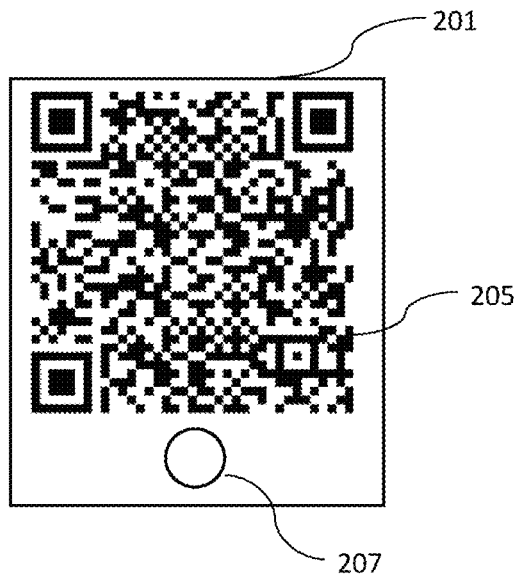
Figure 13:
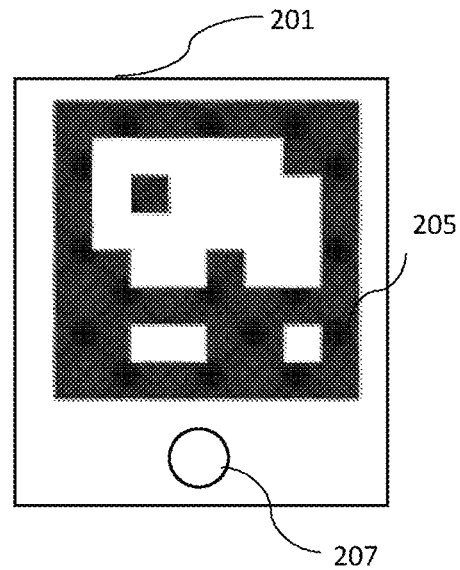

Referring to FIGS. 10 to 13, there are shown example outside surfaces 201 of garments 200 with different forms of visual marker 205 with openings 207 incorporated into or provided alongside the visual markers 205. The openings 207 are not required in all aspects of the present disclosure and are just included as an example. FIGS. 10 and 11 show visual makers 205 in the form of simple icons that are easily understandable to users. FIGS. 12 and 13 show visual markers which comprise machine-readable code. The machine-readable code may comprise an identifier or other information that can be read by a machine. For example, the mobile device 300 may read the machine-readable code using a camera of the mobile device 300. This provides added functionality for the garment 200.

In some examples, the visual marker 205 may act as a fiducial marker 205. A fiducial marker 205 is useable as a point of reference for the garment 200 and thus enables the position of the garment 200 and the motion of the garment 200 over time to be monitored simply by capturing images of the garment 200. In this way, the motion of the wearer of the garment 200 is tracked by determining the location of the fiducial marker 205 in the captured image. The fiducial marker 205 may be in the form of a 2D image. The fiducial marker 205 of the present invention is beneficial as it is simple, of low cost and does not negatively affect the comfort of the garment for the wearer. The fiducial marker may be an augmented reality (AR) marker.

In the example of FIG. 12, the marker 205 is a Quick-Response (QR) code and comprises a visual symbol in the form of black marks upon white pathways. The black marks represent the characters in the code string. The visual symbol may additionally encode redundant information for error detection, correction, and uniqueness over different rotations of the marker.

In the example of FIG. 13, the marker 205 is based on an AR marker 205. The marker 205 comprises a visual symbol in the form of a 6×6 grid of black or white cells which represent 36 binary '0' or '1' symbols. The 36-bit sequence encodes the code string and may additionally encode redundant information for error detection, correction and uniqueness over the different rotations of the marker.

In both examples, the code string/data string may be retrieved from the marker 205 by processing an image containing the visual symbol. It will be appreciated that known image processing operations such as contour extraction and edge detection will be used to read the symbol from the image.

The visual marker 205 may be integrated into the garment 200. The visual marker 205 may be printed onto or into the garment 200. Any known garment printing technique may be used such as screen printing or inkjet printing. The visual marker 205 may be embroidered onto the garment 200.

The visual maker 205 is not limited to the examples described above.

Figure 14:
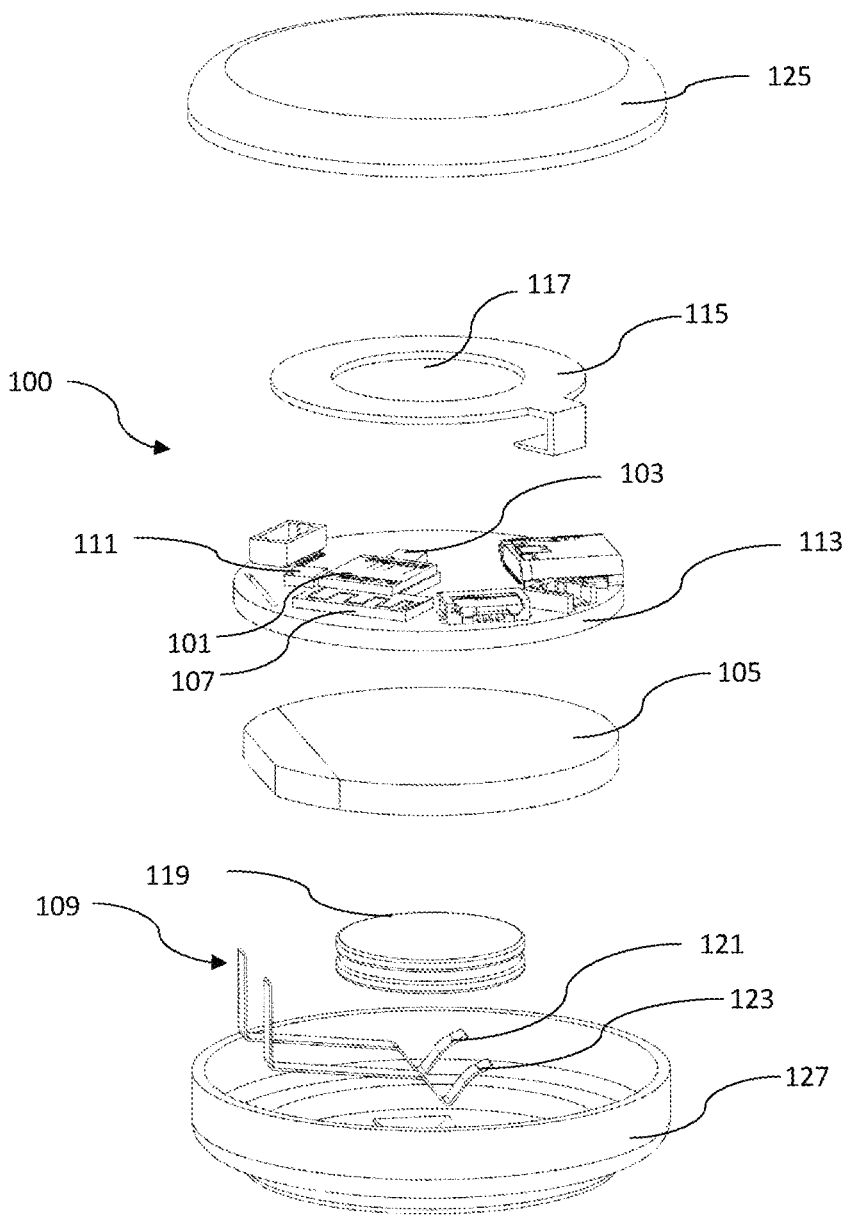
FIG. 14 shows an exploded view of yet another electronics module according to aspects of the present disclosure.

Referring to FIG. 14, there is shown an exploded view of an example electronics module 100 according to aspects of the present disclosure.

The electronics module 100 comprises the processor 101, light source 103, first communicator 107 and electronic component 111 provided on a printed circuit board 113. The power source 105 is provided separately and below the printed circuit board 113. A second communicator 115 in the form of an NFC antenna 115 is also provided. The NFC antenna 115 is positioned above the printed circuit board 113 and comprises an aperture 117 such that the NFC antenna 115 does not obscure light emitted by the light source 103. The electronics module 100 further comprises the interface 109. The interface 109 comprises a magnet 113, and two conductive prongs 115, 117.

The components of the electronics module 100 are provided within a housing formed of a top enclosure 125 and a bottom enclosure 127. The NFC antenna 115 is provided proximate to the top enclosure 125. The bottom enclosure 127 is closest to the body of the wearer in use and the top enclosure 125 is furthest away from the body of the wearer in use. Beneficially, providing the NFC antenna 115 proximate to the top enclosure 125 minimises the communication distance between the NFC antenna 115 and the mobile device 300.

In the example of FIG. 14, the electronic component 111 is in the form of a motion sensor 111 provided on the printed circuit board 113. The motion sensor 111 is arranged to generate a signal in response to detecting an object being brought into contact with the outside surface of the garment in the vicinity of the visual marker. The motion sensor 111 may, in particular, detect a displacement of the electronics module 100 caused by the object being brought into proximity with the electronics module 100. These displacements of the electronics module 100 may be caused by the object being tapped against the electronics module 100. Physical contact between the object and the electronics module 100 is not required as the electronics module 100 may be in a pocket of a garment as described previously. This means that there may be a fabric barrier between the electronics module 100 and the object. In any event, the object being brought into contact with the fabric of the pocket will cause an impulse to be applied to the electronics module 100 which will be sensed by the motion sensor 111. The motion sensor 111 may an inertial measurement unit. The inertial measurement unit may comprise an accelerometer and optionally one or both of a gyroscope and a magnetometer. A gyroscope/magnetometer is not required in all examples, and instead only an accelerometer may be provided or a gyroscope/magnetometer may be present but put into a low power state. A processor of the motion sensor 111 may perform processing tasks to classify different types of detected motion. The processor of the motion sensor 111 may in particular perform machine-learning functions so as to perform this classification. Performing the processing operations on the motion sensor 111 rather than the processor 101 is beneficial as it reduces power consumption, and leaves the processor 101 free to perform other tasks. In addition, it allows for motion events to be detected even when the processor 101 is operating in a low power mode. The detection of the motion event by the sensor 111 can be used to wake-up the processor 101 from the low power mode.

The motion sensor 111 communicates with the controller 103 over a serial protocol such as the Serial Peripheral Interface (SPI), Inter-Integrated Circuit (I2C), Controller Area Network (CAN), and Recommended Standard 232 (RS-232). Other serial protocols are within the scope of the present disclosure. The motion sensor 111 is also able to send interrupt signals to the processor 101 when required so as to transition the processor 101 from a low power model to a normal power mode when a motion event is detected. The interrupt signals may be transmitted via one or more dedicated interrupt pins.

The electronics component 111 may comprise separate or additional sensors 111 for detecting an object being brought into proximity with the electronics module 100. The sensors 111 may comprise a proximity sensor such as the antenna 111. The antenna 115, in this example, is arranged such that a current is induced in the antenna 115 in response to an object being brought into the vicinity of the visual marker. Typically, the object will be a mobile device comprising an antenna which is energized to induce a current in the antenna 115.

The electronics component 111 is not limited to these particular examples. The electronics component 111 may, for example, comprise or be another form of inductive sensor, a capacitive sensor, an optical sensor or an ultrasonic sensor.

Figure 15:
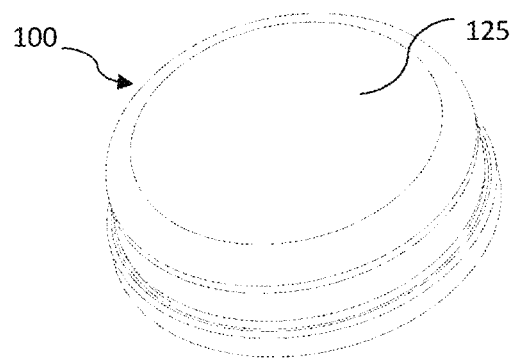
FIGS. 15 and 16 show perspective views of the electronics module of FIG. 14.
Figure 16:
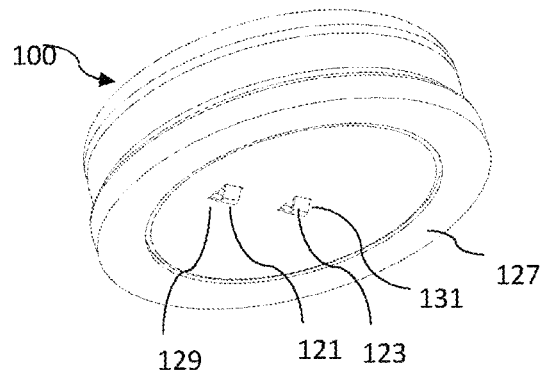

Referring to FIGS. 15 and 16, there is shown an electronics module 100 according to aspects of the present disclosure. The electronics module 100 may be the same as any of the electronics modules 100 as described above in relation to FIGS. 1 to 14. The electronics module 100 comprises a housing which contains the components of the electronics module 100. The housing comprises a top enclosure 125 and a bottom enclosure 127. The bottom enclosure 127 is closest to the body of the wearer in use and the top enclosure 125 is furthest away from the body of the wearer in use. First and second conductive prongs 121, 123 extend from openings 129, 131 in the bottom enclosure 127. The first and second conductive prongs 121, 123 are able to electrically conductively connect with conductive elements provided on a textile so as to electrically conductively connect the electronics module 100 to the conductive elements of the textile. The use of conductive prongs 121, 123 to electrically conductively connect the electronics module 100 to the textile are not required in all aspects of the present disclosure. Other forms of conductive connection may be provided such as via conductive studs or pins. In addition, a conductive connection may not be required as a wireless communication connection may be formed between the electronics module 100 and electronics components of the textile to allow for data exchange between the electronics module 100 and the electronics components of the textile. In one example, the electronics module 100 comprises an NFC coil proximate to the bottom enclosure 127 and the textile material comprises a corresponding NFC coil These NFC coils form a communicative coupling when the electronics module 100 is brought into proximity with the textile to allow for data exchange.

Figure 17:
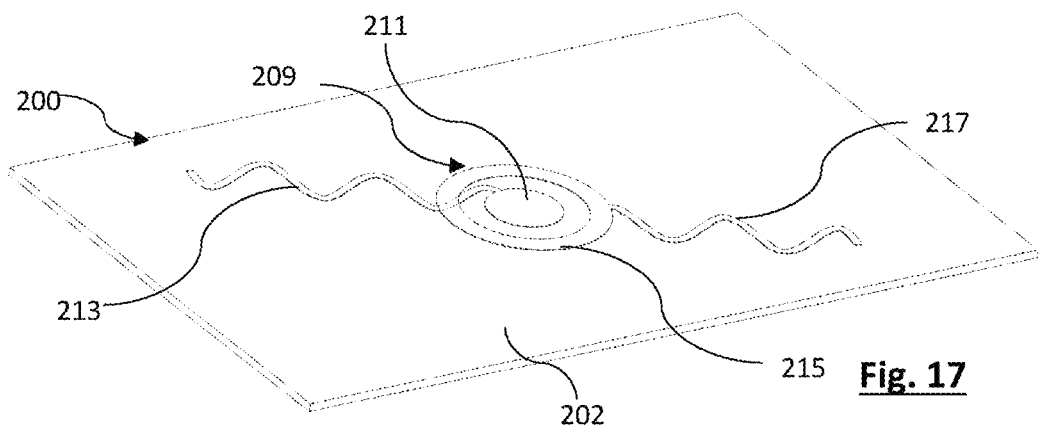
FIG. 17 shows a perspective view of a component of a garment according to aspects of the present disclosure.

Referring to FIG. 17, there is shown an example textile layer of a garment 200 according to aspects of the present disclosure. The garment 200 comprises a textile material 202 and conductive elements 211, 213, 215, 217 provided on the textile material 202. The conductive elements 211, 213, 215, 217 comprise the terminal region 209 of FIGS. 7 and 10. The terminal region 209 comprises a first terminal 211. A first electrically conductive pathway 213 extends from the first terminal 211 to a first electrode (not shown). The first electrically conductive pathway 213 therefore electrically connects the first terminal 211 to the first electrode. The conductive elements 211, 213, 215, 217 further comprise a second terminal 215 and a second electrically conductive pathway 217 that extends from the second terminal 215 to a second electrode (not shown). The second electrically conductive pathway 217 therefore electrically connects the second terminal 215 to the second electrode. The first and second terminals 211, 215 are arranged as concentric circles. A portion of the first electrically conductive pathway 213 extends under the second terminal 215. An insulating layer (not shown) insulates the first electrically conductive pathway 213 from the second terminal 215. This is just one example arranged of electrically conductive pathways on a textile. Other arrangements such as different positioning of electrically conductive pathways, and the use of different materials are within the scope of the present disclosure. For example, the electrically conductive pathways may be formed from a conductive thread or wire. The electrically conductive pathway may be incorporated into the textile. The electrically conductive pathway may be an electrically conductive track or film. The electrically conductive pathway may be a conductive transfer. The conductive material may be formed from a fibre or yarn of the textile. This may mean that an electrically conductive materials are incorporated into the fibre/yarn. In some examples, the conductive pathways may be provided on the underside surface of the textile. In some examples, an aperture may be provided in the textile so as to allow the electronics module to conductively connect to the conductive pathways.

Figure 18:
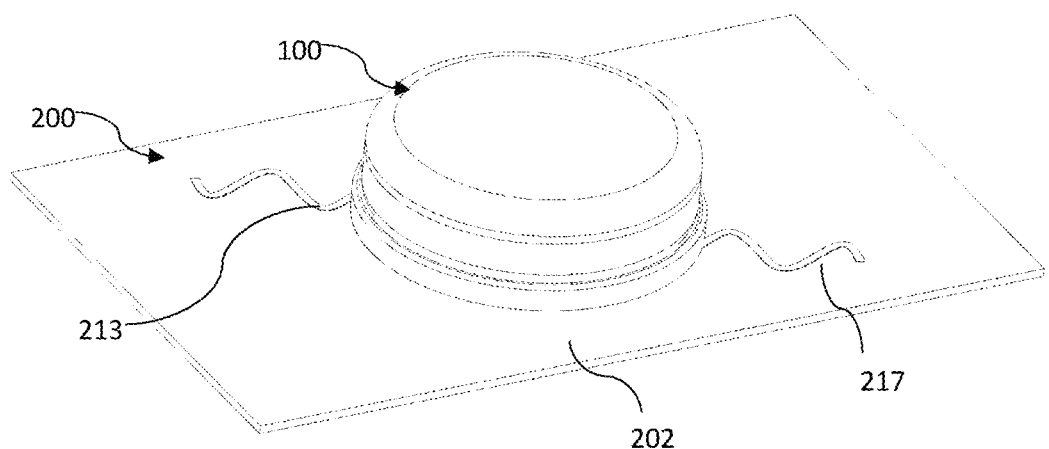
FIG. 18 shows a perspective view of the electronics module of FIGS. 15 and 16 mounted on the garment of FIG. 17.

Referring to FIG. 18, there is shown the electronics module 100 of FIGS. 15 and 16 attached to the garment 200 of FIG. 17. The first conductive prong 121 is brought into conductive electrical contact with the first terminal 211 and the second conductive prong 123 is brought into conductive electrical contact with the second terminal 215. A magnet (FIG. 15, element 119) may be provided in the electronics module 100 and on the underside of the garment 200 so as to maintain the electronics module 100 in releasable attachment with the garment 200.

In the present disclosure, the electronics module may also be referred to as an electronics device or unit. These terms may be used interchangeably.

In summary, there is provided a wearable article 200 comprising an electronics module 100. An electronics module holder 203 holds the electronics module 100. A visual marker 205 is located on an outside surface of the wearable article 200 at a position corresponding to the electronics module holder 203. The module 100 comprises a housing and a processor 101 and electronics component 111 disposed within the housing. The electronics component 111 detects an object being brought into proximity with the electronics module 100. The visual marker 205 indicates the location of the electronics component 111 in the electronics module holder 203. The electronics component 111 generates a signal in response to the object being brought into the vicinity of the visual marker 205. The processor 101 is arranged to receive the signal generated by the electronics component 111 and is arranged to perform an action in response to receiving the signal.

At least some of the example embodiments described herein may be constructed, partially or wholly, using dedicated special-purpose hardware. Terms such as 'component', 'module' or 'unit' used herein may include, but are not limited to, a hardware device, such as circuitry in the form of discrete or integrated components, a Field Programmable Gate Array (FPGA) Application Specific Integrated Circuit (ASIC), or Programmable System-on Chip (PSOC) which performs certain tasks or provides the associated functionality. In some embodiments, the described elements may be configured to reside on a tangible, persistent, addressable storage medium and may be configured to execute on one or more processors. These functional elements may in some embodiments include, by way of example, components, such as software components, object-oriented software components, class components and task components, processes, functions, attributes, procedures, subroutines, segments of program code, drivers, firmware, microcode, circuitry, data, databases, data structures, tables, arrays, and variables. Although the example embodiments have been described with reference to the components, modules and units discussed herein, such functional elements may be combined into fewer elements or separated into additional elements. Various combinations of optional features have been described herein, and it will be appreciated that described features may be combined in any suitable combination. In particular, the features of any one example embodiment may be combined with features of any other embodiment, as appropriate, except where such combinations are mutually exclusive. Throughout this specification, the term "comprising" or "comprises" means including the component(s) specified but not to the exclusion of the presence of others.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings) may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

The invention claimed is:

1. A wearable article, comprising:
   an electronics module holder arranged to hold an electronics module; and
   a visual marker located on an outside surface of the wearable article, the visual marker being located at a position corresponding to the electronics module holder;
   wherein the electronics module comprises:
   a housing;

a processor disposed within the housing;
a first communicator connected to the processor, wherein the first communicator is associated with a first communications protocol; and
a second communicator connected to the processor, wherein the second communicator is associated with a second communications protocol; and
a sensor disposed within the housing, the sensor being arranged to detect a device being brought into proximity with the electronics module,
wherein the visual marker is configured to indicate the location of the sensor of the electronics module when positioned in the electronics module holder such that the device being brought into a vicinity of the visual marker is detectable by the sensor of the electronics module, and
wherein the sensor is arranged to generate a signal in response to the detecting of the device being brought into proximity with the electronics module, wherein the processor is arranged to receive the signal generated by the sensor and is arranged to, in response to receiving the signal:
cause the first communicator to transmit data to the device using the first communication protocol; and
cause the second communicator to establish communications between the electronics module and the device using the second communication protocol, wherein the communications using the second communication protocol is established based on the data transmitted using the first communications protocol.

2. The wearable article as claimed in claim 1, wherein the electronics module holder is provided on an inside surface of the wearable article.

3. The wearable article as claimed in claim 1, wherein the electronics module holder is provided on the outside surface of the wearable article.

4. The wearable article as claimed in claim 1, wherein the electronics module holder comprises a pocket.

5. The wearable article as claimed in claim 1, wherein an inner surface of the electronics module holder is provided with a surface which increases friction between the inner surface and the electronics module when positioned within the electronics module holder.

6. The wearable article as claimed in claim 1, wherein the electronics module is provided with a surface which increases friction between an inner surface of the electronics module holder and the electronics module when positioned within the electronics module holder.

7. The wearable article as claimed in claim 1, wherein the visual marker comprises a machine-readable code.

8. The wearable article of claim 7, wherein the machine-readable code is a QR code.

9. The wearable article as claimed in claim 1, wherein the electronics module further comprises a light source arranged to emit light.

10. The wearable article as claimed in claim 9, wherein the wearable article is constructed such that the light emitted by the light source is visible from the outside surface of the wearable article.

11. The wearable article as claimed in claim 10, wherein the wearable article comprises an opening positioned such that the light emitted by the light source is visible from the outside surface of the wearable article.

12. The wearable article as claimed in claim 10, wherein the wearable article comprises a window constructed from a transparent, translucent, or light-diffracting material.

13. The wearable article as claimed in claim 9, wherein the signal relates to an activity of a user wearing the wearable article, and wherein the processor is configured to process the signal so as to determine whether the activity of the user is within a predetermined allowable range.

14. The wearable article as claimed in claim 13, wherein the light source is configured to emit the light based on the determination by the processor, wherein the emitted light is for indicating to the user whether the activity of the user is within the predetermined allowable range.

15. The wearable article as claimed in claim 1, wherein the electronics module further comprises an optical sensor.

16. The wearable article as claimed in claim 1, wherein the first communication protocol is a near field communication (NFC) communication protocol, and the second communication protocol is a Bluetooth® communication protocol.

17. A wearable article, comprising:
an electronics module holder arranged to hold an electronics module, wherein an inner surface of the electronics module holder is provided with a surface which increases friction between the inner surface and the electronics module when positioned within the electronics module holder, wherein the surface comprises a number of lines or dots of a gripping material; and
a visual marker located on an outside surface of the wearable article, the visual marker being located at a position corresponding to the electronics module holder;
wherein the electronics module comprises:
a housing;
a processor disposed within the housing;
a first communicator connected to the processor, wherein the first communicator is associated with a first communications protocol; and
a second communicator connected to the processor, wherein the second communicator is associated with a second communications protocol; and
a sensor disposed within the housing, the sensor being arranged to detect a device being brought into proximity with the electronics module,
wherein the visual marker is configured to indicate the location of the sensor of the electronics module when positioned in the electronics module holder such that the device being brought into a vicinity of the visual marker is detectable by the sensor of the electronics module, and
wherein the sensor is arranged to generate a signal in response to the detecting of the device being brought into proximity with the electronics module, wherein the processor is arranged to receive the signal generated by the sensor and is arranged to, in response to receiving the signal:
cause the first communicator to transmit data to the device using the first communication protocol; and
cause the second communicator to establish communications between the electronics module and the device using the second communication protocol, wherein the communications using the second communication protocol is established based on the data transmitted using the first communications protocol.

18. The wearable article as claimed in claim 17, wherein the first communication protocol is a near field communication (NFC) communication protocol, and the second communication protocol is a Bluetooth® communication protocol.

19. A wearable article, comprising:
an electronics module holder arranged to hold an electronics module; and
a visual marker located on an outside surface of the wearable article, the visual marker being located at a position corresponding to the electronics module holder;
wherein the electronics module comprises:
a housing;
a processor disposed within the housing;
a first communicator connected to the processor, wherein the first communicator is associated with a first communications protocol; and
a second communicator connected to the processor, wherein the second communicator is associated with a second communications protocol; and
a sensor disposed within the housing, the sensor being arranged to detect a device being brought into proximity with the electronics module,
wherein the visual marker is configured to indicate the location of the sensor of the electronics module when positioned in the electronics module holder such that the device being brought into a vicinity of the visual marker is detectable by the sensor of the electronics module, and
wherein the sensor is arranged to generate a signal in response to the detecting of the device being brought into proximity with the electronics module, wherein the processor is arranged to receive the signal generated by the sensor and is arranged to in response to receiving the signal:
change an operational mode of the electronics module;
cause the first communicator to transmit data to the device using the first communication protocol; and
cause the second communicator to establish communications between the electronics module and the device using the second communication protocol, wherein the communications using the second communication protocol is established based on the data transmitted using the first communications protocol.

20. The wearable article as claimed in claim 19, wherein the first communication protocol is a near field communication (NFC) communication protocol, and the second communication protocol is a Bluetooth® communication protocol.

* * * * *